(12) United States Patent
Bergmeier et al.

(10) Patent No.: US 8,153,817 B2
(45) Date of Patent: Apr. 10, 2012

(54) SYNTHESIS OF METHYL NONACTATE DERIVATIVES

(75) Inventors: Stephen C. Bergmeier, Athens, OH (US); Nigel D. Priestley, Alberton, MT (US)

(73) Assignee: Ohio University, Athens, OH (US)

( * ) Notice: Subject to any disclaimer, the term of this patent is extended or adjusted under 35 U.S.C. 154(b) by 136 days.

(21) Appl. No.: 12/441,140

(22) PCT Filed: Sep. 11, 2007

(86) PCT No.: PCT/US2007/078095
§ 371 (c)(1), (2), (4) Date: Oct. 20, 2009

(87) PCT Pub. No.: WO2008/035793
PCT Pub. Date: Mar. 20, 2008

(65) Prior Publication Data
US 2010/0056779 A1    Mar. 4, 2010

Related U.S. Application Data

(60) Provisional application No. 60/843,856, filed on Sep. 12, 2006.

(51) Int. Cl.
*C07D 249/00* (2006.01)

(52) U.S. Cl. .................................................. 548/255
(58) Field of Classification Search .................. 548/255
See application file for complete search history.

(56) References Cited

U.S. PATENT DOCUMENTS

2004/0241799 A1    12/2004    Shen et al.
2006/0154967 A1    7/2006    Ehrenfreund et al.

OTHER PUBLICATIONS

Nikodinovic, et al., Org. Lett., 2006, vol. 8(3), pp. 443-445.*
International Search Report of the ISA for PCT/US2007/78095, mailed Aug. 4, 2008.
Written Opinion of the ISA for PCT/US2007/78095, mailed Aug. 4, 2008.
International Preliminary Report on Patentability for PCT/US2007/78095, issued Mar. 17, 2009.

* cited by examiner

*Primary Examiner* — Susannah Chung
(74) *Attorney, Agent, or Firm* — Calfee, Halter & Griswold LLP

(57) ABSTRACT

Methyl nonactate is converted into a variety of different triazoloamide antibacterial agents by a reaction scheme involving (1) inversion of the secondary alcohol of the methyl nonactate to produce the corresponding azidoester, (2) converting the azido ester to the corresponding azidoamide, and (3) converting the azido group of the azidoamide to a triazole to produce the corresponding triazoloamide.

6 Claims, No Drawings

SYNTHESIS OF METHYL NONACTATE DERIVATIVES

CROSS-REFERENCE TO RELATED APPLICATION

This application claims the benefit of U.S. provisional patent application Ser. No. 60/843,856, entitled SYNTHESIS OF METHYL, NONACTATE DERIVATIVES and filed Sep. 12, 2006, the entire disclosure of which is fully incorporated herein by reference.

BACKGROUND AND SUMMARY

Nonactin is a macrotetrolide natural product that Promiliad Biopharma isolates from *Streptomyces* fermentation. While nonactin itself has a number of uses, it can be readily converted to methyl nonactate by methanolysis (e.g., reaction with methanol and HCl). In accordance with this invention, methyl nonactate can be converted into distinct classes of antibacterial agents, namely triazoloamides and triazolocarboxylates, according to the following general reaction schemes

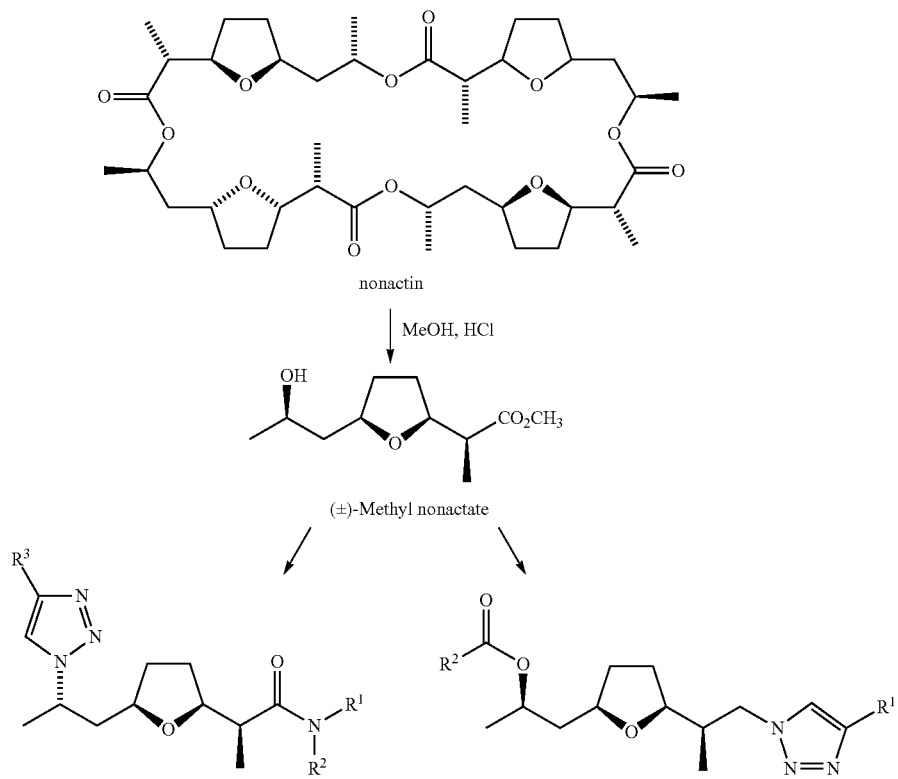

DETAILED DESCRIPTION

The Triazoloamides

In accordance with one aspect of this invention, methyl nonactate is converted into a variety of different triazoloamide antibacterial agents by a reaction scheme involving
(1) inversion of the secondary alcohol of the methyl nonactate to produce the corresponding azidoester,
(2) converting the azido ester to the corresponding azidoamide, and
(3) converting the azido group of the azidoamide to a triazole to produce the corresponding triazoloamide.

A particular example of this reaction scheme is given below:

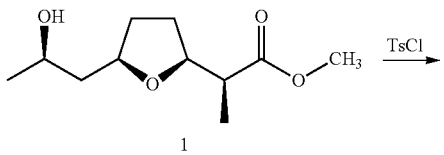

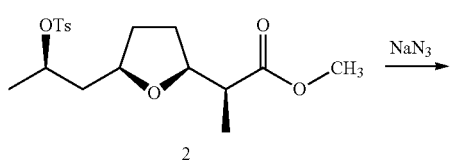

-continued

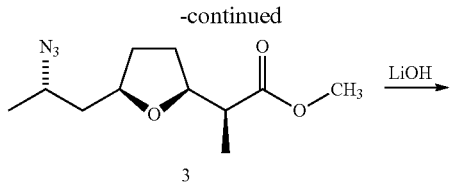

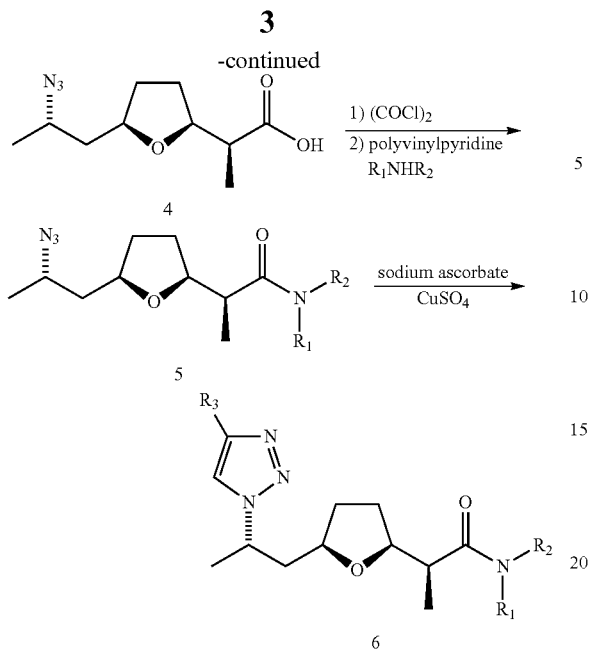

An example of each synthesis that can be used in this reaction scheme is given below:

Synthesis of 2 (Tosylate). To a solution of methyl nonactate, 1, (100 mg, 0.46 mmol) in DCM (1 mL) pyridine (0.11 mL, 1.38 mmol) was added followed by tosyl chloride (0.13 g, 0.69 mmol) under inert atmosphere and stirred in room temperature for 24 h. The reaction mixture was concentrated in vacuum and chromatographed (22% Ethylacetate-Hexane) to afford pure tosylate (130 mg, 84%).

Synthesis of 3 (Amidoester). Sodium azide (0.23 g, 3.5 mmol) was added to a solution of tosylate 2 (0.12 g, 0.35 mmol) in DMF (2 mL) and heated to 50° C. for 6 h. Reaction mixture was diluted with water (2 mL) and extracted with ethyl acetate (2×8 mL). Combined organic extract was washed with water (3×1 mL), NaHCO₃ (2×2 mL) and brine (2×1 mL). Solvent was removed under vacuum and chromatographed (20% Ethyl acetate-Hexane) to afford pure azido ester 3 (80 mg, 94%).

Synthesis of 4 (Azidoacid). To a solution of azidoester 3 (0.8 g, 3.31 mmol) in THF-H₂O (1:1, 16 mL) LiOH. H₂O (1.4 g, 33.1 mmol) was added into it and stirred for 24 h in room temperature. Diluted with ethyl acetate and washed with 1% NaOH solution (2×4 mL). The combined aqueous extract was cooled to 0° C. and acidified with 2M HCl until acidic and extracted with ethyl acetate (2×15 mL), washed with brine (2×2 mL), dried over magnesium sulfate and concentrated to afford pure azidoacid 4 (0.45 g, 60%).

Synthesis of 5 (Azidoamide). Oxalyl chloride (0.8 mL, 9.34 mL) was added to a solution of azidoacid 4 (0.45 g, 1.87 mmol) benzene (6 mL) and the solution was heated to 50° C. for 2 h. Reaction mixture was concentrated in vacuum and the crude material (0.45 g, 98%) was used for the next step without any further purification. IR (Neat): 2976, 2939, 2877, 1790, 1456 Cm⁻¹.

Poly vinyl pyridine (2% cross linked, 0.063 g, 0.6 mmol) was added to a solution of azido acid chloride (0.03 g, 0.12 mmol) in DCM (0.5 mL) and amine (0.12 mmol) was added into it. Resulting solution was stirred in inert atmosphere for 24 h. Ethyl acetate was added and filtered through a small pad of silica gel to afford the amide 5 (55-70% yield).

Synthesis of 6 (Triazoloamide). A solution of alkyne (110 mg, 0.051 mmol) in t-BuOH—H₂O (1:1, 0.5 mL) was added to an azido amide 5 (16 mg, 0.046 mmol) and was shaken for 2 minutes in a mechanical shaker. Sodium ascorbate (1M, 0.014 mL, 0.014 mmol) followed by copper sulfate (1M, 0.046 ml, 0.046 mL) was added and was shaken additional 16-24 hours. Reaction mixture was diluted with ethyl acetate (15 mL), washed with aqueous ammonium hydroxide (1:1) solution (2×1 mL), brine (2×1 mL) and dried over magnesium sulfate. Removal of solvent under reduced pressure afforded the triazole product 6 (24 mg) in 96% yield.

Other analogous syntheses can be used in place of these particular syntheses. In addition, other specific reaction schemes for converting methyl nonactate to the desired triazoloamide via the corresponding azido ester and azido amide can also be used.

The triazoloamides of this invention have the general formula:

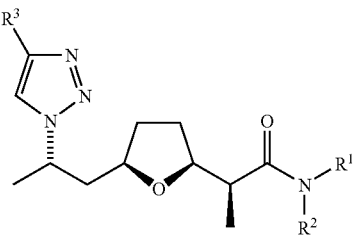

where $R^1$, $R^2$ and $R^3$ may be, H, $C_1$-$C_{12}$ aliphatic or aromatic groups such as alkyl, alkenyl and the like, 5 or 6 membered rings, condensed polynuclear aliphatic or aromatic 5 or 6 membered rings, these rings optionally containing one or more N or O heteroatoms or both, such rings also being optionally substituted with various pendant groups including $C_1$-$C_{12}$ aliphatic and aromatic hydrocarbon groups, $C_1$-$C_{12}$ ethers and the like. Specific $R^1$, $R^2$ and $R^3$ moieties are:

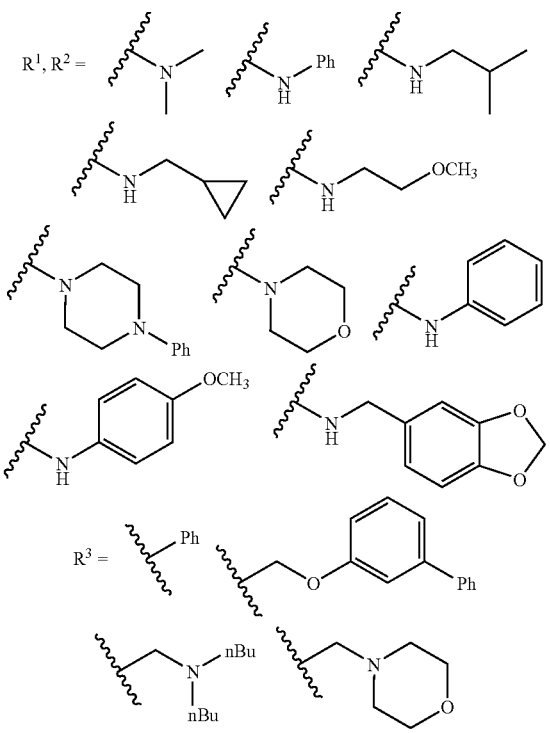

-continued

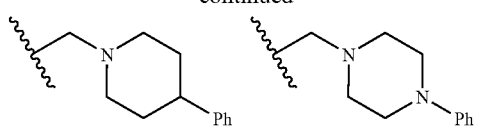

These triazoloamides exhibit significant antibacterial properties against a wide range of gram positive and gram negative bacteria. For example, at least one of these compounds demonstrated an MIC of 250 μM against *B. subtilis* (a gram positive bacteria). In comparison ampicillin, which is an antibiotic in wide therapeutic use, has an MIC of 100 μM in this screen. Preliminary tests also show that these compounds kill gram negative (*E. coli*) as well as gram positive bacteria. From a safety perspective, these compounds do not harm MCF-10 cells (normal cells).

Specific triazoloamides of this invention and their associated MIC values are:

TABLE 1

MIC Values of Selected Triazoloamides

| Compound | MIC/μM |
|---|---|
|  | 250 |
|  | 500 |
|  | 1000 |
|  | 1000 |
|  | 1000 |

TABLE 1-continued

MIC Values of Selected Triazoloamides

| Compound | MIC/μM |
|---|---|
| [structure: phenyl-piperazine-CH2-triazole-CH(CH3)-CH2-tetrahydrofuran-CH(CH3)-C(O)NH-cyclopentyl] | 2000 |
| [structure: phenyl-piperazine-CH2-triazole-CH(CH3)-CH2-tetrahydrofuran-CH(CH3)-C(O)-morpholine] | 2000 |
| [structure: phenyl-piperazine-CH2-triazole-CH(CH3)-CH2-tetrahydrofuran-CH(CH3)-C(O)NH-cyclohexyl] | 2000 |
| [structure: phenyl-triazole-CH(CH3)-CH2-tetrahydrofuran-CH(CH3)-C(O)N(CH3)2] | 4000 |
| [structure: phenyl-piperazine-CH2-triazole-CH(CH3)-CH2-tetrahydrofuran-CH(CH3)-C(O)-piperazine-phenyl] | 4000 |

The Triazolocarboxylates

In accordance with another aspect of this invention, methyl nonactate is converted into a variety of different triazolocarboxylate antibacterial agents by a reaction scheme involving (1) reducing the ester moiety of the methyl nonactate to produce the corresponding diol, (2) converting the primary alcohol moiety of the corresponding diol to an azido group to produce the corresponding azidoalcohol, (3) converting the remaining alcohol of the corresponding azidoalcohol to a carboxylate to produce the corresponding azidocarboxylate, and (4) converting the azido group of the corresponding azidocarboxylate to a triazole group to produce the target triazolocarboxylate A particular example of this reaction scheme is given below:

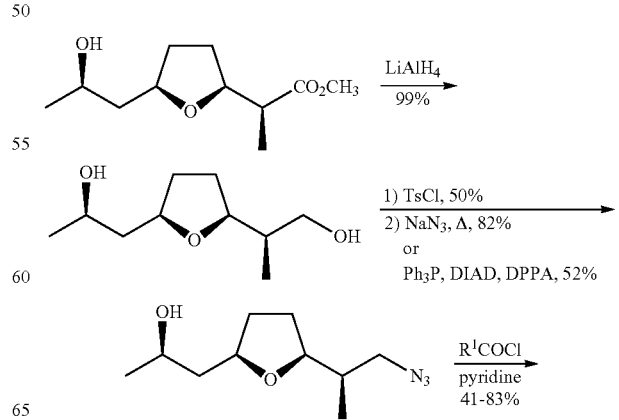

-continued

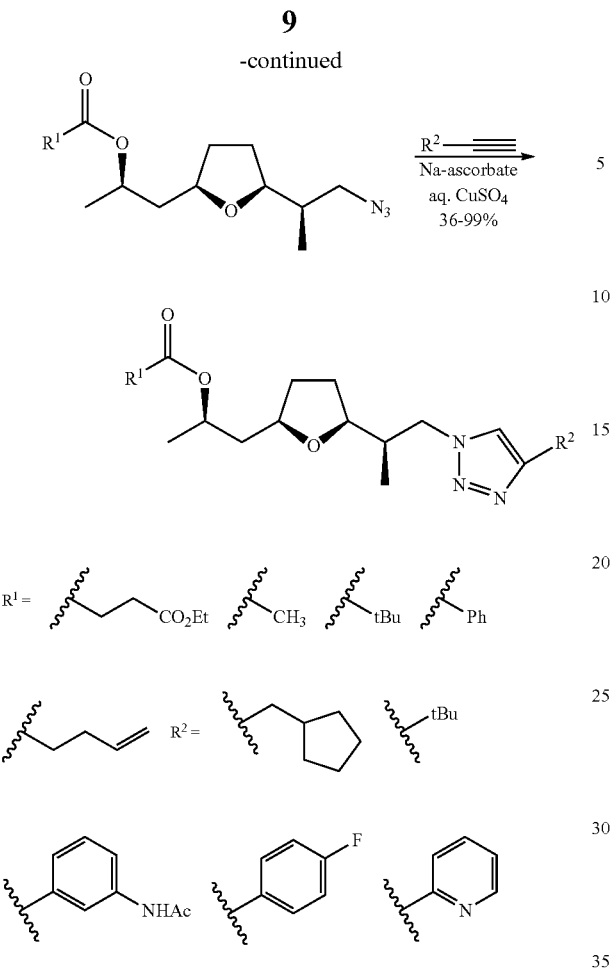

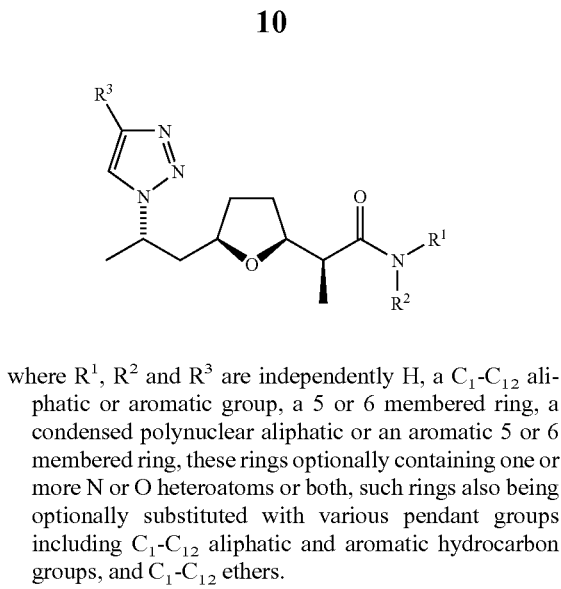

where $R^1$, $R^2$ and $R^3$ are independently H, a $C_1$-$C_{12}$ aliphatic or aromatic group, a 5 or 6 membered ring, a condensed polynuclear aliphatic or an aromatic 5 or 6 membered ring, these rings optionally containing one or more N or O heteroatoms or both, such rings also being optionally substituted with various pendant groups including $C_1$-$C_{12}$ aliphatic and aromatic hydrocarbon groups, and $C_1$-$C_{12}$ ethers.

2. A triazoloamide of the formula

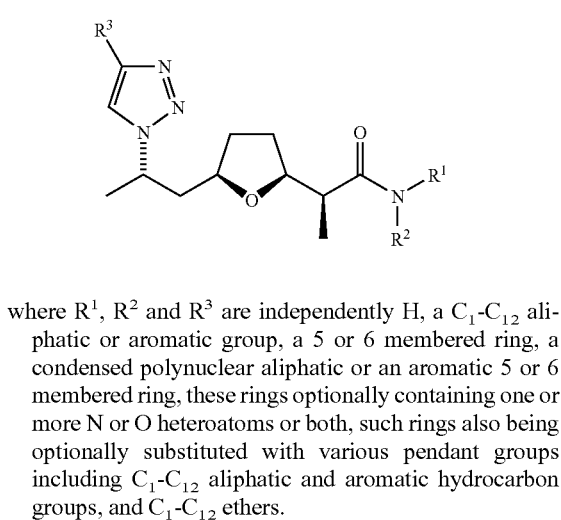

where $R^1$, $R^2$ and $R^3$ are independently H, a $C_1$-$C_{12}$ aliphatic or aromatic group, a 5 or 6 membered ring, a condensed polynuclear aliphatic or an aromatic 5 or 6 membered ring, these rings optionally containing one or more N or O heteroatoms or both, such rings also being optionally substituted with various pendant groups including $C_1$-$C_{12}$ aliphatic and aromatic hydrocarbon groups, and $C_1$-$C_{12}$ ethers.

3. The triazoloamide of claim 2, wherein

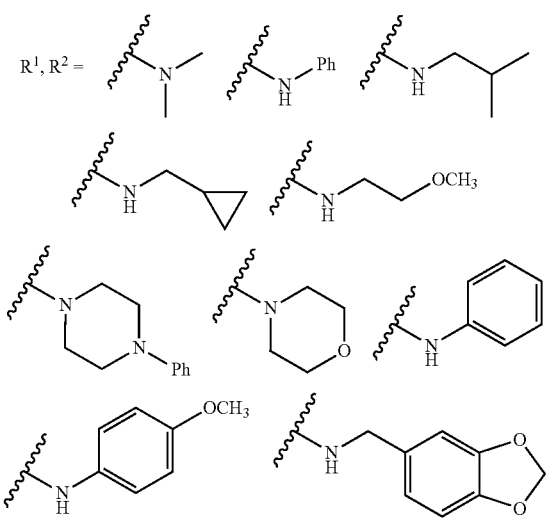

Other analogous reaction schemes for converting methyl nonactate to the desired triazolocarboxylate via the corresponding diol, azidoalcohol and azidocarboxylate can also be used. In addition, the desired triazolocarboxylates can include other $R^1$ and $R^2$ groups including H, $C_1$-$C_{12}$ aliphatic or aromatic groups such as alkyl, alkenyl and the like, 5 or 6 membered rings, condensed polynuclear aliphatic or aromatic 5 or 6 membered rings, these rings optionally containing one or more N or O heteroatoms or both, such rings also being optionally substituted with various pendant groups including $C_1$-$C_{12}$ aliphatic and aromatic hydrocarbon groups, $C_1$-$C_{12}$ ethers and the like.

As in the case of the triazoloamides discussed above, these triazolocarboxylates are also believed to exhibit significant antibacterial properties against a wide range of gram positive and gram negative bacteria and also not to harm MCF-10 cells (normal cells).

The invention claimed is:

1. A process for converting methyl nonactate into a triazoloamide antibacterial agent comprising
   (1) inverting the secondary alcohol of the methyl nonactate to produce the corresponding azidoester,
   (2) converting the azido ester to the corresponding azidoamide, and
   (3) converting the azido group of the azidoamide to a triazole to produce the corresponding triazoloamide, wherein the triazoloamide is of the formula -continued

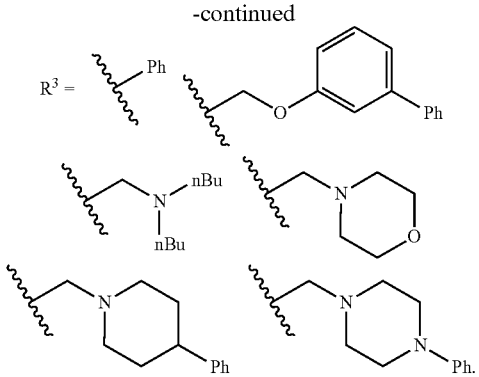

4. A process for converting methyl nonactate into a triazolocarboxylate antibacterial agent comprising
   (1) reducing the ester moiety of the methyl nonactate to produce the corresponding diol,
   (2) converting the primary alcohol moiety of the corresponding diol to an azido group to produce the corresponding azidoalcohol,
   (3) converting the remaining alcohol of the corresponding azidoalcohol to a carboxylate to produce the corresponding azidocarboxylate, and
   (4) converting the azido group of the corresponding azidocarboxylate to a triazole group to produce the target triazolocarboxylate, wherein the triazolocarboxylate is of the formula

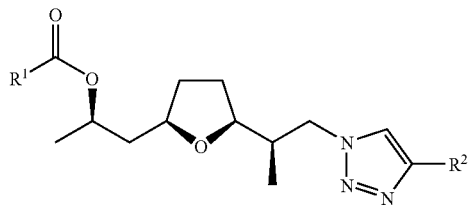

wherein $R^1$ and $R^2$ are independently H, a $C_1$-$C_{12}$ aliphatic or aromatic group, a 5 or 6 membered ring, a condensed polynuclear aliphatic or an aromatic 5 or 6 membered ring, these rings optionally containing one or more N or O heteroatoms or both, such rings also being optionally substituted with various pendant groups including $C_1$-$C_{12}$ aliphatic and aromatic hydrocarbon groups, and $C_1$-$C_{12}$ ethers.

5. A triazolocarboxylate of the formula

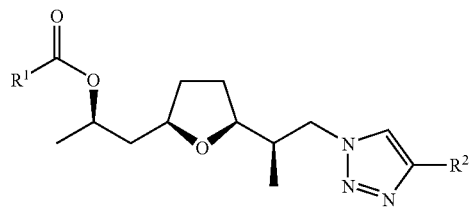

wherein $R^1$ and $R^2$ are independently H, a $C_1$-$C_{12}$ aliphatic or aromatic group, a 5 or 6 membered ring, a condensed polynuclear aliphatic or an aromatic 5 or 6 membered ring, these rings optionally containing one or more N or O heteroatoms or both, such rings also being optionally substituted with various pendant groups including $C_1$-$C_{12}$ aliphatic and aromatic hydrocarbon groups, and $C_1$-$C_{12}$ ethers.

6. The triazolocarboxylate of claim 5, wherein $R^1$ and $R^2$ are independently selected from

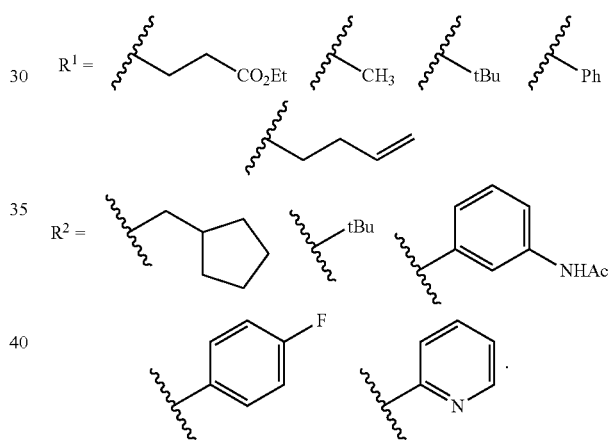

* * * * *